United States Patent [19]

Muldoon

[11] Patent Number: Plant 6,595

[45] Date of Patent: Feb. 7, 1989

[54] BEDDING VIOLA NAMED 'BLACK MAGIC'

[76] Inventor: Jackson P. Muldoon, 29870 Mill Creek Rd., Sheridan, Oreg. 97378

[21] Appl. No.: 82,296

[22] Filed: Aug. 6, 1987

[51] Int. Cl.[4] ..... H01H 5/00

[52] U.S. Cl. ..... Plt./68

[58] Field of Search ..... Plt./68

*Primary Examiner*—Robert E. Bagwill

[57] ABSTRACT

New and distinct cultivar of bedding viola named Black Magic, characterized by its prominent black colored flowers, floriferous habit, hardiness to extreme cold and compact stature.

1 Drawing Sheet

1

My new variety of Viola plant originated as a chance sport stem in a self-perpetuating ornamental bedding Viola planting in Sheridan, Oreg. during July of 1984. The parent plant which exhibited the black flowering sport stem was a blue flowering variety of unknown origin. Since the discovery of the new Viola cultivar named Black Magic, I have asexually reproduced it by the rooting of stem cuttings of terminal growth, finding that all the characteristics described here are firmly fixed and hold true through successive generations of asexual reproduction.

The illustration shows the novel blossom color and compact growth habit.

The following is a detailed description of my new variety of Viola based on observations made in my greenhouses and out of doors at my nursery in Sheridan, Oreg. All colors are according to the R.H.S. Colour Chart published by The Royal Horticultural Society of London, England.

Plant:

*Name.*—Black Magic

*Origin.*—Sport stem from a blue seedling form of Viola tricolor. Form: Low, compact, spreading. Height: 7.5 cm. Growth: slow to moderate. Type of cuttings: Terminal stem. Rooting time: 10–14 days starting during the second week in March over 21C bottom heat. Rooting habit: Fibrous.

2

Foliage:

*Arrangement.*—Alternate simple.

*Shape.*—Ovate to lanceolate.

*Base.*—Cuneate.

*Margin.*—Crenate.

*Size.*—Blade and petiole: 4 cm; length of blade: 2.5 cm; width of blade at widest point: 1.5 cm.

*Color.*—Leaf blade — bottom: 146B top: 146B. Veins — bottom and top: 144B. Petiole — bottom and top: 144B.

Flower:

*Form.*—Solitary, perfect, actinomorphic, nearly obicular.

*Borne.*—Terminally on upright stems.

*Stem length.*—5 cm.

*Size of mature flower.*—Length: 3.0 cm, Width: 2.5 cm.

*Color.*—Petal — 202A. Center or "eye" — 9A.

Blooming habit.—Relative number: profuse. Time of flowering: March 15 through November 15.

I claim:

1. A new and distinct form of Viola plant as described and illustrated known by the cultivar name Black Magic and particularly characterized by its black flowers; floriferous habit; low growing, compact and spreading form; ability to thrive heartily in full sun and its hardiness to severely cold Winter temperatures.

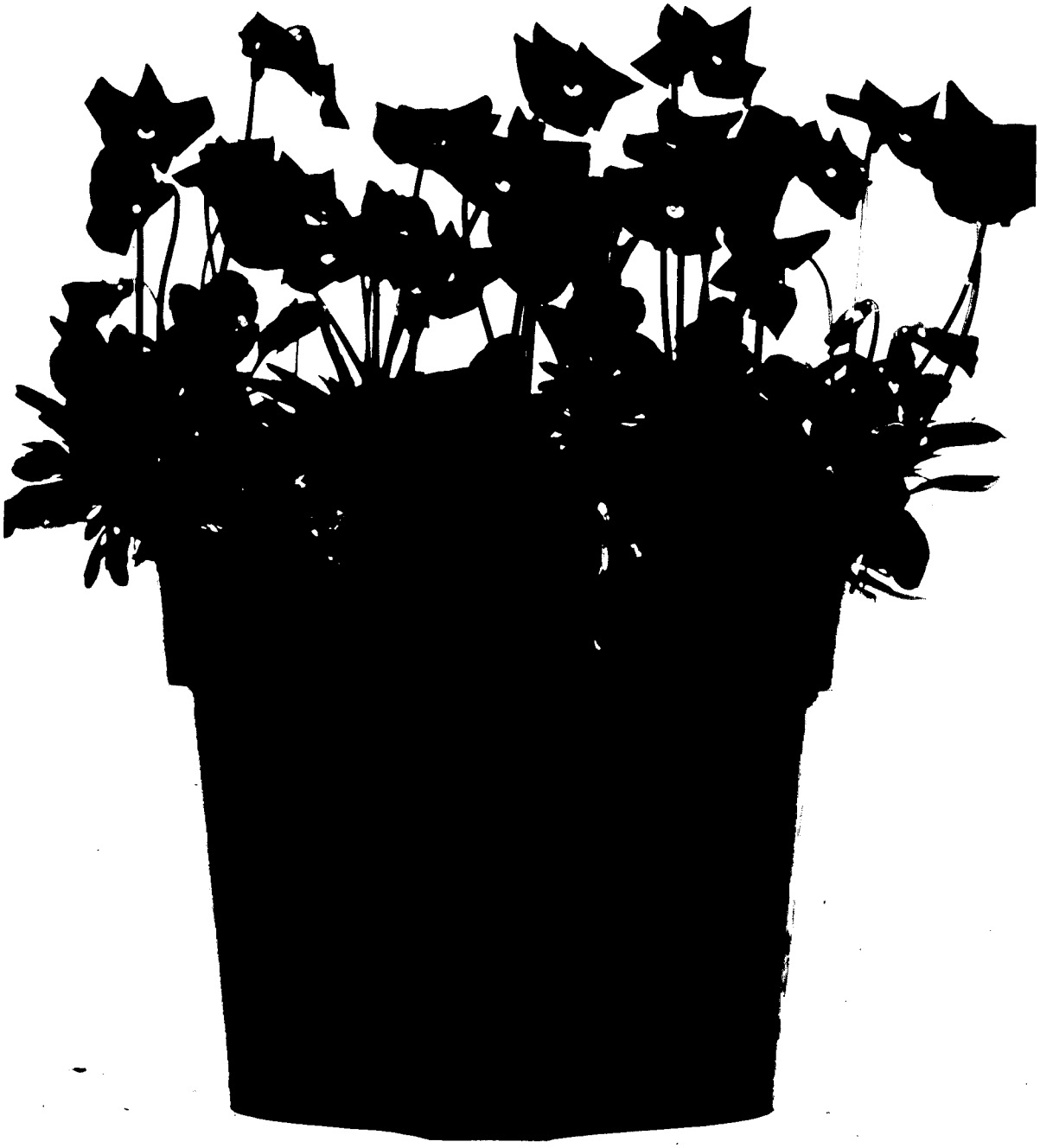

* * * * *